US006579433B2

United States Patent
Bernstein et al.

(10) Patent No.: US 6,579,433 B2
(45) Date of Patent: Jun. 17, 2003

(54) ELECTROCHEMICAL MEASURING CELL FOR DETECTING HYDROCYANIC ACID

(75) Inventors: Christoph Bernstein, Lübeck (DE); Andreas Nauber, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 73 days.

(21) Appl. No.: 09/971,759

(22) Filed: Oct. 9, 2001

(65) Prior Publication Data

US 2002/0043458 A1 Apr. 18, 2002

(30) Foreign Application Priority Data

Oct. 14, 2000 (DE) ......................... 100 51 106

(51) Int. Cl.$^7$ ............................. G01N 27/26
(52) U.S. Cl. ................ 204/415; 204/412; 204/431; 204/432
(58) Field of Search ..................... 204/412, 415, 204/431, 432

(56) References Cited

U.S. PATENT DOCUMENTS

| | | | | |
|---|---|---|---|---|
| 3,859,191 A | * | 1/1975 | Frant et al. .................. 204/415 |
| 4,659,434 A | * | 4/1987 | Driscoll et al. .............. 204/415 |
| 4,756,804 A | * | 7/1988 | Driscoll et al. .............. 204/415 |
| 5,041,204 A | | 8/1991 | Kühn et al. ................... 204/415 |
| 5,565,075 A | * | 10/1996 | Davis et al. .................. 204/431 |
| 5,997,706 A | | 12/1999 | Kiesele et al. ............... 204/415 |
| 6,074,539 A | * | 6/2000 | Deininger et al. ........... 204/415 |

* cited by examiner

Primary Examiner—Bruce F. Bell
(74) Attorney, Agent, or Firm—Walter Ottesen

(57) ABSTRACT

An electrochemical measuring cell for detecting hydrocyanic acid is improved in such a manner that a stable measurement signal is provided after a short time. The measuring cell includes a measuring electrode (1) of sintered gold and a counter electrode (2). A measuring cell housing (4) accommodates the measuring electrode (1) and the counter electrode (2). An electrolyte is in the measuring cell housing (4) and includes sulphuric acid with an additive of silver sulphate. A diffusion membrane (5) is disposed between the measuring electrode (1) and the substance to be detected.

6 Claims, 1 Drawing Sheet

ELECTROCHEMICAL MEASURING CELL FOR DETECTING HYDROCYANIC ACID

FIELD OF THE INVENTION

The invention relates to an electrochemical measuring cell for detecting hydrocyanic acid in a gas sample.

BACKGROUND OF THE INVENTION

An electrochemical measuring cell of the above kind is disclosed in U.S. Pat. No. 5,041,204. This electrochemical measuring cell includes a measuring cell housing filled with sulphuric acid as an electrolyte. A measuring electrode, a counter electrode and a reference electrode are disposed in the measuring cell housing and are of gold. The electrolyte contains an additive of copper (II) sulphate. The measuring cell housing is closed to the ambient by a membrane permeable to gas. The gas to be detected reaches the measuring electrode through the membrane. The copper catalyst, which is added to the electrolyte, makes possible a direct anodic oxidation of the cyanide to dicyanogen without the electrode material being consumed. Because of the copper additive, the detecting reaction takes place as an oxidation only with the participation of the dissolved copper with HCN in the electrolyte solution. The measuring electrode establishes the electrical contact to the electrolyte solution.

It is disadvantageous in the known measuring cell that the measurement signal reaches a stable end value only after several minutes when the measuring cell is exposed to hydrocyanic acid and this makes handling during a measuring operation difficult. For example, the calibration is very time consuming. Furthermore, the measurement signal drifts when exposed to hydrocyanic acid over a long time.

U.S. Pat. No. 5,997,706 discloses an electrochemical measuring cell wherein the electrodes are of gold and are mounted in a measuring cell housing which is filled with sulphuric acid as an electrolyte. The electrolyte contains an additive of silver sulphate in a saturated solution. The known electrochemical measuring cell is suitable for detecting hydride gases, especially phosphine and arsine; however, the measuring cell does not provide a useable measurement signal when exposed to hydrocyanic acid.

SUMMARY OF THE INVENTION

It is an object of the invention to improve upon an electrochemical measuring cell for detecting hydrocyanic acid in such a manner that a stable measurement signal is provided after a short time.

The electrochemical measuring cell of the invention is for detecting hydrocyanic acid. The electrochemical measuring cell includes: a housing having an opening directed toward the ambient containing the hydrocyanic acid to be detected and defining an electrolyte chamber; an electrolyte contained in the chamber; a measuring electrode and a counter electrode disposed in the chamber so as to be in spaced relationship to each other; a diffusion membrane permeable to the hydrocyanic acid and mounted between the measuring electrode and the ambient; the measuring electrode being made of sintered gold; and, the electrolyte including sulphuric acid and an additive of silver sulphate.

It has been surprisingly shown that an electrochemical measuring cell, which has a measuring electrode of sintered gold and sulphuric acid as an electrolyte with an additive of silver sulphate, provides a stable measurement signal when exposed to hydrocyanic acid. The measuring electrode has a large surface because of its configuration as a gold-sinter electrode. With the presence HCN, the measurement electrode dissolves while forming AuCN. The decomposition of the measuring electrode is supported by the presence of silver ions in the electrolyte.

In contrast, a measuring electrode, which is configured as a gold thin-layer electrode, does not supply a useable measurement signal because the surface is too small for the reaction with HCN. In contrast to the known electrochemical measuring cell for detecting hydrocyanic acid, the measuring electrode in the measuring cell according to the invention is consumed by the electrochemical reaction, which takes place in the measuring cell, in the manner of a fuel cell.

The preferred thickness of the measuring electrode is greater than 100 micrometer. A thickness in the range between 100 micrometers and 200 micrometers supplies good measuring results. The measuring electrode is so manufactured that gold particles having a small grain size are held together with a hydrophobic binding agent so that gas channels are present between the gold particles. PTFE is suitable and preferred as a binding agent. The measuring electrode is preferably located directly behind a PTFE diffusion membrane through which the component, which is to be detected, reaches the measuring electrode.

The grain size is important because, in this way, a specific surface can be adjusted on the measuring electrode for the electrochemical reaction within the measuring cell. If the grain size is too large, then the effective surface is too small. The range for the grain size of the gold particles preferably lies between 5 micrometers and 50 micrometers.

The counter electrode preferably is of gold. Other suitable materials are iridium, rhodium and platinum.

A stable electrochemical potential within the electrochemical measuring cell can be adjusted with a reference electrode between the measuring electrode and the counter electrode. Gold, iridium and platinum are suitable materials for the reference electrode.

It has been surprisingly shown that the measuring cell according to the invention is, in addition to hydrocyanic acid, also suitable for detecting $NO_2$.

BRIEF DESCRIPTION OF THE DRAWING

The invention will now be described with reference to the single FIGURE (FIG. 1) of the drawing which is a side elevation view, in section, of a measuring cell according to an embodiment of the invention.

DESCRIPTION OF THE PREFERRED EMBODIMENTS OF THE INVENTION

Figure 1:
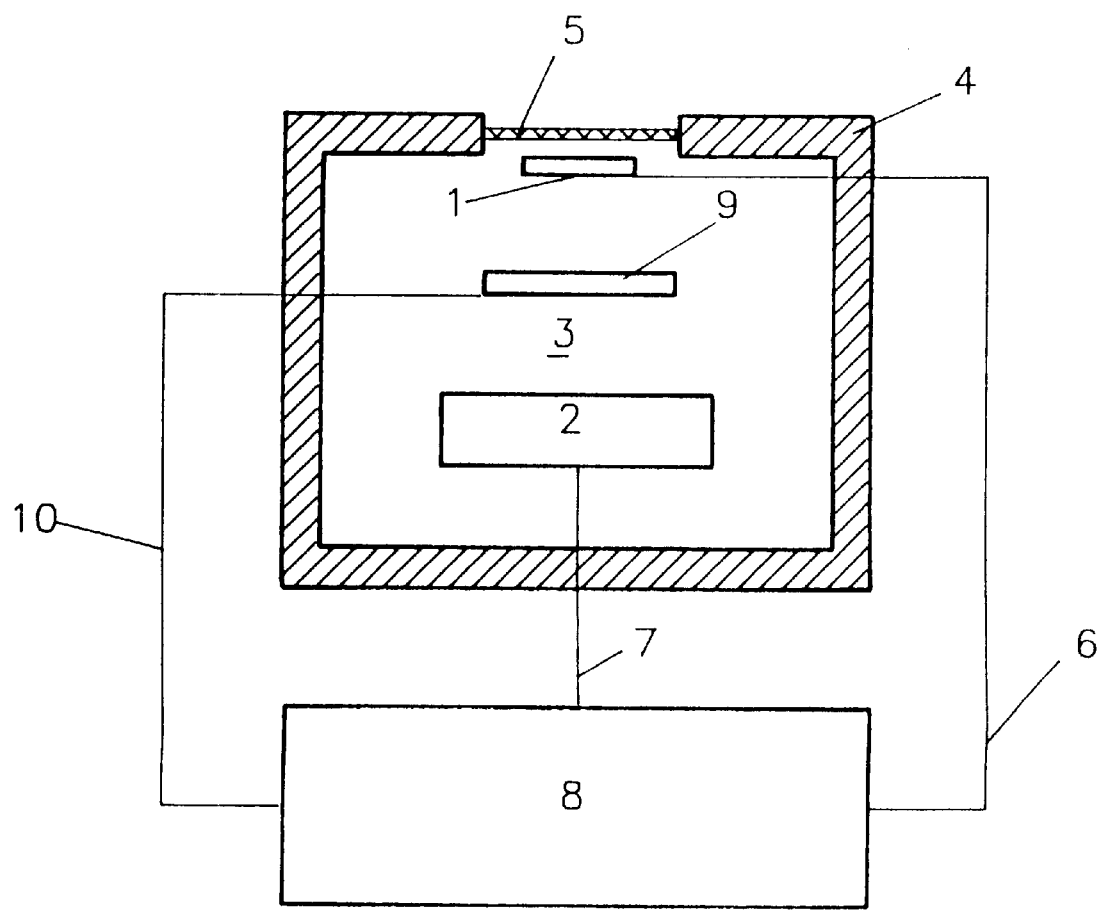

FIG. 1 shows an electrochemical measuring cell having a measuring electrode 1 of sintered gold, a counter electrode 2 and a reference electrode 9 which are likewise of gold in an electrolyte chamber 3 of a measuring cell housing 4. The electrolyte chamber 3 is filled with an aqueous solution of 4M sulphuric acid with an electrolyte additive of silver sulphate. The ambient contains the gas sample with hydrocyanic acid and the electrolyte chamber 3 is closed off with respect to the ambient by a diffusion membrane 5 permeable to hydrocyanic acid as well as to $NO_2$. The measuring electrode 1, the counter electrode 2 and the reference electrode 9 are provided with respective measuring leads (6, 7, 10), which are lead through the housing 4 and are connected to an evaluation unit 8 for further processing of the measurement signal. The measuring electrode 1 is located directly behind the diffusion membrane 5. For more clarity, the measuring electrode 1 is shown at a distance to the diffusion membrane 5.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for detecting hydrocyanic acid, the electrochemical measuring cell comprising:
    a housing having an opening directed toward the ambient containing the hydrocyanic acid to be detected and defining an electrolyte chamber;
    an electrolyte contained in said chamber;
    a measuring electrode and a counter electrode disposed in said chamber so as to be in spaced relationship to each other;
    a diffusion membrane permeable to said hydrocyanic acid and mounted between said measuring electrode and the ambient;
    said measuring electrode being made of sintered gold; and, said electrolyte including sulphuric acid and an additive of silver sulphate.

2. The electrochemical measuring cell of claim 1, wherein said measuring electrode has a thickness greater than 100 micrometers.

3. The electrochemical measuring cell of claim 1, wherein said measuring electrode has a thickness between 100 micrometers and 200 micrometers.

4. The electrochemical measuring cell of claim 1, wherein said sintered gold comprises gold particles having a grain size lying in a range of 5 to 50 micrometers.

5. The electrochemical measuring cell of claim 4, wherein said gold particles are held together with a hydrophobic binding agent so that gas channels are present between said gold particles.

6. The electrochemical measuring cell of claim 1, wherein said diffusion membrane is also permeable to $NO_2$ and said electrochemical measuring cell is also suitable for detecting $NO_2$.

* * * * *